United States Patent [19]

Litt et al.

[11] Patent Number: 5,091,963
[45] Date of Patent: Feb. 25, 1992

[54] METHOD AND APPARATUS FOR INSPECTING SURFACES FOR CONTRAST VARIATIONS

[75] Inventors: Maria Litt, Cleveland Heights; Wesley N. Cobb; David C. Bond, both of University Heights; Jack C. Chung, Cincinnati, all of Ohio; Gary G. Leininger, Rolla, Mo.

[73] Assignee: The Standard Oil Company, Cleveland, Ohio

[21] Appl. No.: 189,452

[22] Filed: May 2, 1988

[51] Int. Cl.$^5$ .............................................. G06K 9/00
[52] U.S. Cl. ...................................... 382/8; 358/101; 358/106; 358/107
[58] Field of Search ...................... 358/101, 106, 107; 356/71, 402; 382/8, 43, 48

[56] References Cited

U.S. PATENT DOCUMENTS

| | | | |
|---|---|---|---|
| 4,547,987 | 10/1985 | Peterson | 356/402 |
| 4,669,123 | 5/1987 | Kobayashi et al. | 582/8 |
| 4,670,779 | 6/1987 | Nagano | 356/402 |
| 4,736,851 | 4/1988 | Ricros et al. | 358/106 |
| 4,771,468 | 9/1988 | Batchelder et al. | 382/8 |
| 4,823,194 | 4/1989 | Mishima et al. | 358/101 |
| 4,881,269 | 11/1989 | Billiotte et al. | 382/8 |

OTHER PUBLICATIONS

Rosenfeld, Azriel, "Edge Detection", *Digital Picture Processing*, Academic Press, Chapters 10.2 and 11.3, pp. 84–96 and 240–257.
Galbraith, "Automated Detection of Wafer Surface Defects by Laser Scanning", Silicon Processing, ASTM STP 804, Gupta, ed., ASTM (1983) pp. 492–500.
Green, "Overview of Surface Defect Detection Systems", Northern New England Chapter of I.E.S. (1984).
Inspex, Inc., Undated Data Sheets for W1515-2, W1616, W1990, W1996, EX1500, EX1992, Wafer Inspection Systems.
Martin et al., "Optical Scanning of Silicon Wafers For Surface Contaminants", Electro-Optical Systems Design (Sep. 1980) pp. 45–49.
Harris, et al., "Wafer Inspection Automation; Current and Future Needs," Solid State Tech. (Aug. 1983) pp. 199–205.
"SEMs for Semiconductor Inspection and CD Measurements", Solid State Technology (Jun. 1983) pp. 37–38.
Baker, "Semiconductor Wafer Inspection", SPIE vol. 480 Integrated Circuit Metrology II (1984) pp. 14–21.
Gara, "Automatic Microcircuit and Wafer Inspection", Electronics Test pp. 60–70.
Harris et al., "Process Controlled by Automated in-Process Wafer Inspection", SPIE vol. 470 Optical Microlithography III pp. 253–260.

Primary Examiner—David K. Moore
Assistant Examiner—Jose L. Couso
Attorney, Agent, or Firm—Larry W. Evans; Joseph G. Curatolo

[57] ABSTRACT

A method of and apparatus for inspecting the surface of an article for isolated contrast variations by illuminating the surface, forming an image of the surface from the reflected light, the image being composed of pixels that contain digitized information indicative of the relative intensity level of light reflected from a particular portion of the surface, comparing the intensity levels of at least some of the pixels to a predetermined intensity threshold to identify portions of the surface contrasting with other portions of that surface, and determining from the identified pixels the number of isolated contrast variations on the surface and the area of each of the variations. The number and size of the contrast variations appearing on the inspected article surface are compared to acceptability criteria to decide whether the article is acceptable for a particular use or in particular channels of commerce.

29 Claims, 4 Drawing Sheets

METHOD AND APPARATUS FOR INSPECTING SURFACES FOR CONTRAST VARIATIONS

FIELD OF THE INVENTION

The invention concerns an automated method of, and apparatus for, inspecting surfaces, particularly unpolished surfaces, to identify the number of, and areas of, isolated contrast variations on the surfaces. The invention particularly concerns the formation of an image of a surface comprising electronic signals and the searching of that image to identify isolated contrast variations and their respective areas. The invention is particularly applicable to the inspection of wafers employed in the semiconductor industry.

BACKGROUND

In various manufacturing processes articles are prepared that may include isolated areas of contrast variations on their exposed surfaces. These isolated contrast variations may be attributable to inhomogeneities within the materials. That is, the surfaces may contain spots or streaks on a background of essentially uniform color and/or hue. In many cases, these contrast variations have no deleterious effect upon the use articles for an intended purpose. However, if a surface contains a sufficient number of contrast variations or the respective quantities and areas of the variations exceed predetermined standards, the articles may not be considered acceptable in some commercial channels. In order to meet a particular industry's cosmetic or performance standards, it is necessary to inspect each article for contrast variations before it is shipped to a consumer. The articles may be visually inspected by a properly trained human. Generally, a human inspector requires substantial training and the inspection results are always subjective. Therefore it is desirable to employ an automated apparatus and method that performs an objective inspection of surfaces for contrast variations.

Surface inspection methods and apparatus are particularly useful in the semiconductor industry. There, some automated apparatus and methods for inspecting polished surfaces of semiconductor wafers, such as silicon and gallium arsenide, are known. Generally, those surfaces are searched for three dimensional features, such as scratches, etch pits and foreign particles, i.e., defects, rather than for two dimensional contrast variations. That apparatus is generally expensive and usually employs a scanning laser light source or an ultraviolet light source. The known apparatus exploits the mirror-like properties of the polished surface in searching for defects. Therefore, this apparatus is not able to search an unpolished surface for defects or to search any type of surface for contrast variations.

The surface of many articles useful in industrial processes are never polished. Therefore, the known automated inspection apparatus and methods cannot be used to locate defects or contrast variations on the surface of those articles. An example of articles used in the semiconductor industry that are not polished, but which must be inspected, are wafers that are employed as dopant sources for doping silicon semiconductor wafers. However, the invention and its application is not limited or restricted to articles of a particular shape, composed of any particular element, compound of mixture or intended for a particular use.

Accordingly, it is an objective of the invention to devise an apparatus and to achieve an automated method for objectively inspecting a surface of an article for isolated contrast variations. It is a further objective of the invention that the inspection method permit acceptance or rejection of inspected surfaces according to established criteria concerning the number of contrast variations and their respective areas that may acceptably appear on an exposed surface.

SUMMARY OF THE INVENTION

In the invention, a method for inspecting a surface of an article for isolated contrast variations includes illuminating the surface, forming a surface image of the article from the light reflected from the article surface, the surface image being composed of a plurality of pixels, each pixel consisting of a digitized electrical signal indicative of a particular portion of the article surface and the relative intensity of the light reflected from that portion, comparing the intensity levels of at least some of the pixels to a predetermined threshold intensity level to identify the pixels corresponding to portions of the article contrasting with other portions of that surface, determining from the identified pixels the number of the isolated contrast variations on the article surface and the area of each of those variations, and applying acceptability criteria based on the number of contrast variations and their respective areas to decide whether an article is acceptable for a particular use.

In a preferred embodiment, the intensity levels of the pixels in the surface image are corrected to compensate for non-uniformities in the illumination of the article surface. Most preferably, the pixels forming the surface image are organized in orthogonal rows and columns. In one embodiment of the invention, the intensity levels of the pixels are corrected by fitting the intensities along some rows or columns, taken individually, to a polynomial distribution, subtracting from the intensity level of each pixel in the particular row or column, the intensity level predicted by the distribution, and adding an average intensity level to difference intensity level obtained from the subtraction.

In another embodiment, the intensity level of the pixels in each row or column are normalized to the intensity level of the first pixel in that row or column and the normalized intensity levels are convolved with a smoothing, low pass filter. The resulting, convolved light intensity distribution along the row or column is subtracted from the corresponding pixel to produce the desired correction. An average intensity level may be added to the smoothed intensity level obtained in the subtraction.

The locations of areas of contrast variations on a surface are preferably determined by comparing the intensities of one or more pixels to a threshold intensity. In one embodiment of the invention, an edge threshold is calculated as each pixel in a row or column is sequentially examined. The edge threshold is calculated from the intensities of pixels near or adjacent to a pixel of interest. The edge threshold identifies abrupt contrast changes. The intensity of a pixel of interest is compared to the edge threshold and a threshold detector is activated when the pixel intensity falls on a preselected side of the edge threshold. The threshold detector applies a second threshold test to determine whether a contrast variation is present or not.

In another embodiment of the invention, the surface image is segmented into regions including both row and column pixels and the mean and standard deviation of the intensity levels of the pixels in each region are calculated. In addition, the difference between the most frequently occurring and mean intensity levels in each region is calculated as a difference intensity level for comparison to a predetermined difference threshold. The standard deviation of the intensity levels in each region is compared to a second predetermined, deviation threshold. If the absolute value of the difference intensity level and standard deviation of the intensity levels for a region both fall on preselected sides of their respective thresholds, the region is identified as including pixels representing a contrast variation on the surface.

Once the pixels corresponding to isolated contrast variations on the surface are identified, the area of each variation can be determined by counting the number of pixels within it. The number of contrast variations and the area of each of them can be compared to established acceptability criteria for the maximum number of acceptable isolated variations, considering the area of each variation. The results of the comparison decide whether the article is acceptable for a particular purpose. Articles that are unacceptable for one purpose can be directed to another purpose for which they are acceptable or can be discarded if none of the established criteria are met.

In a preferred apparatus for carrying out the novel method, light is directed from a source so as to illuminate the surface of an article and a video camera is employed to form an image of the article surface. Preferably, the article is disposed on a background of uniform hue that produces a background image having a strong contrast with the surface image produced by the light reflected from the article. The pixels corresponding to the background image and, preferably, the article edge adjacent the background image, are discarded from further consideration in searching the surface image for contrast variations.

DETAILED DESCRIPTION OF PREFERRED EMBODIMENTS

The invention is described below with reference to a particular embodiment and application. In that application, a generally planar, but unpolished, surface of a thin article, i.e. a wafer, is inspected. The inspected surface must reflect at least some of the light used to illuminate the surface. That is, the surface must be at least partially opaque to the inspecting light. Otherwise, the invention may be applied to inspect the surface, polished or unpolished, planar or non-planar, of other articles besides wafers, to detect the presence and size of isolated contrast variations.

APPARATUS

Figure 1:
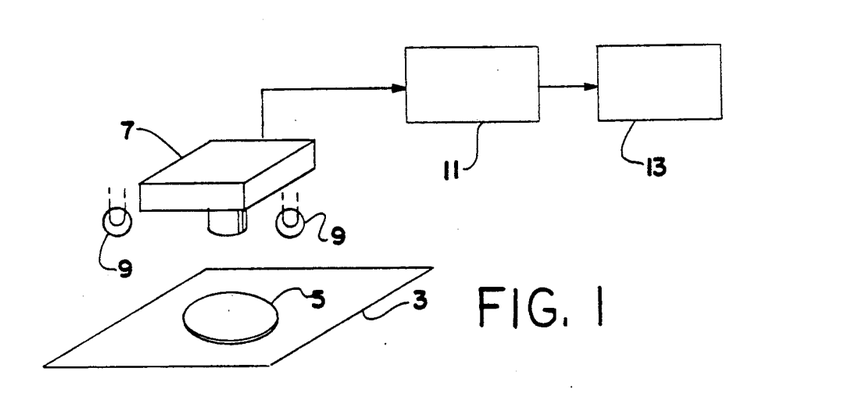
FIG. 1 is a schematic view of apparatus for carrying out one application of the novel method.

In FIG. 1 an apparatus for carrying out one application of the novel method, inspection of a wafer surface, is schematically shown. There, a support surface 3 is provided upon which a wafer 5 is disposed. Preferably, support 3 is of a hue selected to give a strong contrast with the hue of wafer 5. For example, if wafer 5 is generally dark in color, support 3 may be white. Suspended above wafer 5 is a camera 7 for producing an image of the light reflected from background 3 and wafer 5. That light is provided by an artificial light source, indicated by two lamps 9 suspended above wafer 5, but positioned so that light does not directly enter the lens of camera 7. Camera 7 may be a charge coupled device (CCD) camera or a vidicon type camera.

Regardless of the type of video camera employed, it produces an electronic image, i.e. an image in the form of electronic signals. Generally, this initial electronic image is in an analog form. The analog image is scanned horizontally and vertically in a preselected pattern. Intensity information is obtained by sampling the magnitude of the analog image during the scans. The sampled magnitudes are digitized. The sequence of the sampling provides location information that is combined with the corresponding digitized intensity information to form a plurality of pixels i.e., a digital image. The digitized intensity information is generally referred to a gray scale that has number of steps, e.g. 256, that range from a "black" to a "white" intensity at opposite ends of the gray scale. In this description, the term intensity level generally interchangably refers to a step on the gray scale employed.

The intensity levels of the pixels are preferably adjusted, as a whole, so that a useful range of the available gray scale steps are used. For example, when the gray scale includes 256 steps, a term may be added to or subtracted from each pixel intensity so that the average pixel intensity lies at about the 170th step. Generally, it is desirable the average pixel lie at about two thirds of the maximum gray level step. However, depending upon the amplitude of the intensity variations, different ranging considerations may be applied.

Where the pixels are organized in rows and columns, the image position information is conveniently treated as consisting of two subscripts, one indicating the row and the other indicating the column of the position. This digital information is conveniently manipulated in a computer using established matrix algebra techniques. For simplicity, some of the steps in the novel process are generally described and claimed here with respect to rows of pixels. The same techniques are equally applicable to processing columns of pixels. Therefore, it is understood that the description and claims referring to rows of pixels are equivalent to similar steps involving columns of pixels.

The signal information obtained from camera 7 is digitized in a video processor 11. The digitized video information from processor 11 is supplied to a computer 13 for contrast variation searching and for determination of the inspection results. Computer 13 may include an output device, such as a printer or a CRT. In addition, computer 13 may be interfaced with electromechanical apparatus for placing and removing wafers 5 on background 3 and for sorting inspected wafers in accordance with the results of the inspection.

Generally, the contrast variations sought to be detected in the course of an inspection of wafer 5 are quite small. Because of the slight differences in the intensities of light reflected from the reference and contrast areas of wafer 5, it is important that the incident light intensity across the surface of the wafer be as uniform as possible. To achieve that goal, it is preferred that a planar source of light, rather than point sources like lamps 9, be employed to illuminate the surface of wafer 5.

Figure 2:
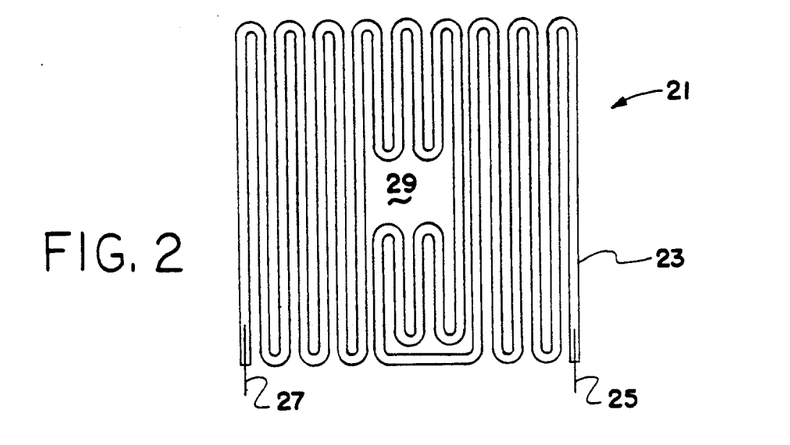
FIG. 2 is a front view of a light source that is particularly useful in one application of the novel method.

In FIG. 2, a planar light source 21 found useful in carrying out the novel method is shown in a front view. Light source 21 includes a sealed hollow tube 23 disposed in a plane. Tube 23 includes numerous generally parallel segments to produce a uniform illumination as nearly as possible. Tube 23 at its sealed ends contains electrodes 25 and 27 so that gas within the tube can be electrically excited. Essentially, light source 21 is a fluorescent lamp of complex shape. Light source 21 contains an opening 29 in its center so that the lens of camera 7 can be inserted through that opening. With the lens of camera 7 inserted in opening 29, only light reflected from background 3 and wafer 5 enters the lens. We have found that reasonably uniform illumination can be obtained if light source 21 has a dimension along each of its sides that is about three times the dimension of the side of the area desired to be uniformly illuminated.

In order to apply the invention as described here, several different types of cameras were tested. Two CCD video cameras produced grainy pictures and showed a large gray scale variation from the center to the edges of an image of a uniform wafer. A vidicon tube video camera produced a noisy picture and one on which the gray level difference across the image was not smooth. Satisfactory performance was obtained with a Newvicon video camera, an improved vidicon-type camera, manufactured by MTI/Dage. While some gray level variation between the middle and edge of the image formed was observed, the variation in gray levels was smooth. The Newvicon video camera includes anti-blooming compensation circuitry that can produce some variations in light detection characteristics, particularly between different inspections. However, satisfactory performance with this camera was achieved.

The Newvicon camera produced an analog image that was processed in a Gould-DeAnza general purpose image processing apparatus. The Gould-DeAnza apparatus includes both hardware and software and was used to produce a "square" image composed of 512 pixels on a side with a 256 step gray scale. The digital image information was supplied to a DEC Microvax II computer for identification of contrast variations, determination of the are of each variation and comparison of those results to acceptability criteria.

LOCATION OF ARTICLE BOUNDARIES

In FIG. 1, wafer 5 is shown as having a generally circular shape. Wafers employed in semiconductor device processing generally have circular cross sections. However, the invention is not restricted to use with articles having generally circular or any other shape. Regardless of the shape of the wafer, it will have a peripheral edge. The illumination falling on background 3 and on wafer 5 is reflected into camera 7. The light intensity information corresponding to background 3 is of no value in identifying contrast variations on the surface of wafer 5. Therefore it is desirable to identify light intensity information corresponding to background 3, i.e. the background image, and to discard it so that only light intensity information from wafer 5, i.e. the wafer or surface image, is employed to find contrast variations. By discarding information corresponding to the background image, the computational time required to evaluate information corresponding to the wafer image can be substantially reduced.

Known methods of edge detection may be employed to find the boundaries of a wafer. For example, the intensity levels of the pixels in one or more columns and/or rows may be sequentially compared to determine the position at which the intensity levels change abruptly, indicating a wafer edge. Mathematical techniques for edge detection in digital images are well-known. A preferred edge detection technique employs scanning across rows and columns of pixels and comparing intensity values using so-called central difference operators. That technique is described in Digital Picture Processing, volume 2, by Rosenfeld and Kak (1982) at pp. 84-96, the disclosure of which is incorporated herein by reference. The central difference operators measure the rate of change of intensities by comparing the intensities of pixels lying on either side of a pixel of interest. Pixel location is conveniently designated by subscripts i and j. For a row scan, i.e. a constant i, the central difference operator calculates the gray scale rate of change value in accordance with Equation (1).

$$g'(i,j) = g(i,j+1) - g(i,j-1) \qquad (1)$$

The maximum and minimum points of g obtained from the central difference operator calculation indicate pixels lying at the edge of a wafer. If the geometric shape of a wafer is known, only a limited number of edge pixels need to be located in order to determine the approximate location of the entire periphery of the wafer. This shape information can be advantageously used to minimize the number of rows and/or columns of pixels that must be examined to determine the location of the wafer edge or edges, saving computational time.

Figure 3:
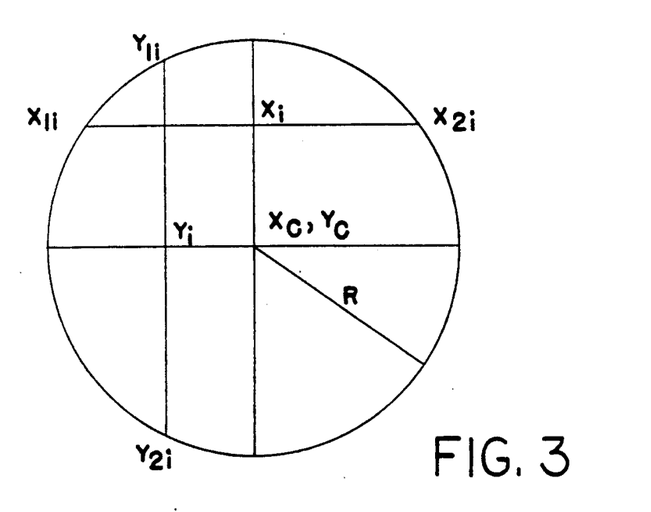
FIG. 3 is an illustration of a determination of the location of the edges of a circular wafer, i.e. the location of the wafer image, according to one embodiment of the invention.

Circular Wafers. FIG. 3 illustrates the process of locating the entire periphery of a circular wafer by examining the intensity levels of pixels in only one column and one row. As can be seen from FIG. 3, the points identified on the horizontal scan as edges of the wafer are $x_{1i}$ and $x_{2i}$. Likewise, on the vertical scan, the edge points identified are $y_{1i}$ and $y_{2i}$. Horizontal and vertical chords are drawn in FIG. 3 between the identified edge points. The midpoints of the two chords, $x_i$ and $y_i$, lie along diameters of the circular wafer. The midpoints of these chords are, in fact, the coordinates $x_c$ and $y_c$, of the center of a perfectly circular wafer. The radius of the wafer is calculated from the distance between the wafer center $x_c$, $y_c$ and any of the end points of the two chords. Once the radius and center of the circular wafer are known, the location of the wafer periphery is determinable. From that information, the background image pixels can be identified and discarded from further consideration in locating contrast variations in the wafer image.

In practice, a nominally circular wafer may not be perfectly circular nor may the edge pixels exactly identify the periphery of the wafer. To allow for that situation, it is desirable to examine several rows and columns of pixels and to calculate an average wafer center location from the locations of the edge pixels determined in each examination. In our experience, when the contrast between the wafer and background is relatively strong, only a few horizontal and the vertical examinations are necessary to determine the location of the center and the radius of a circular wafer accurately. In inspecting white wafers, we prefer to employ a black background. In that situation, we have found that examining ten rows and ten columns of equally spaced pixels from an image consisting of 512 pixels on the side is sufficient to determine accurately the position the entire periphery of a circular wafer.

Non-circular Wafers. If a wafer has a non-circular, but known, geometrical shape, such as a square or rectangle, then the location of the edges of that wafer can also be simplified. The intensity levels of pixels are sampled along a minimum number of rows and columns to locate some edge pixels. Using that location data and the known shape of the wafer, the entire periphery of the wafer can be determined without examining all of the background and wafer image pixels.

Some pixels in a wafer, i.e. surface, image lying on or very near the edge of a wafer contain unreliable intensity information. We have found it useful, in some instances, to discard pixels lying within ten pixels of a wafer edge to avoid considering potentially unreliable intensity information. Some detail is lost if these pixels are discarded and, obviously, any contrast variations lying near the edge of a wafer will go undetected or will be reported with smaller areas than actually exist. This compromise between reliability of the results of the method and the precision of those results should be chosen based on the particular application made of the method.

CORRECTION OF ILLUMINATION NON-UNIFORMITIES

The isolated contrast variations that are sought to be detected usually contrast very weakly with the remainder of the article surface. As a result, the process of identifying the isolated variations is susceptible to noise from a variety of sources. One potential source of noise is slight non-uniformities in the illumination that falls on the surface of the wafer. In spite of the measures to produce highly uniform illumination that have already been described, slight non-uniformities in lighting cannot be completely eliminated. Therefore it is useful, in some embodiments of the invention, to correct the intensity levels of the pixels in order to remove noise or noise-like effects attributable to non-uniformities in illumination.

Figure 5:
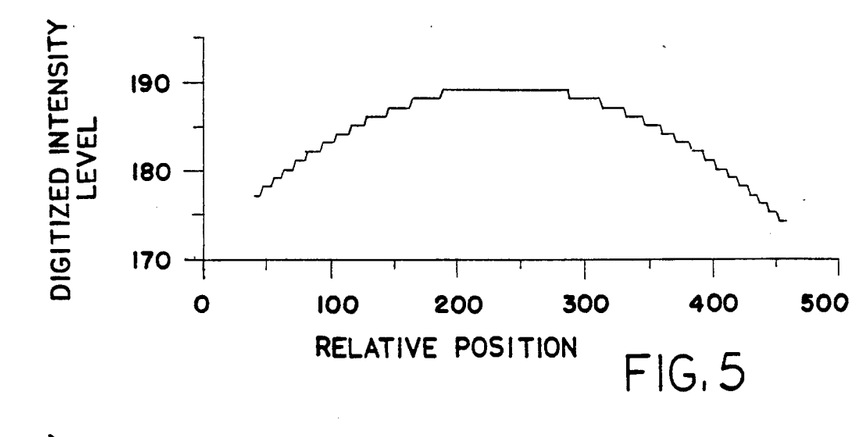
FIG. 5 is a graph of an estimated distribution of digitized intensity levels for pixels in a row calculated from the data of FIG. 4.
Figure 6:
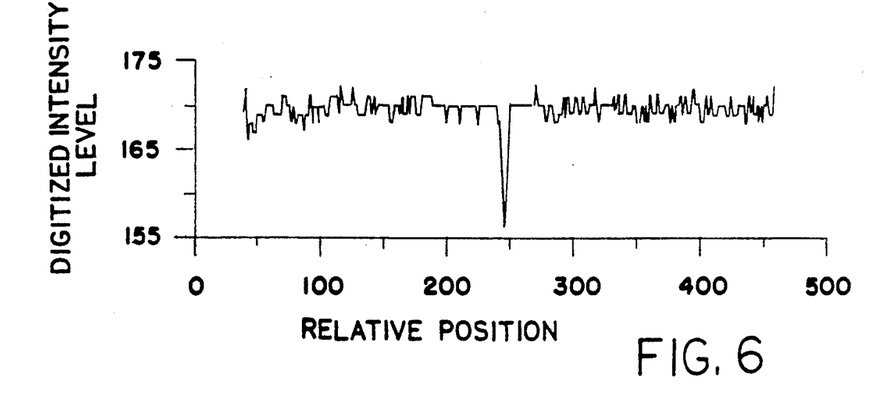
FIG. 6 is a graph of corrected, digitized intensity level information for pixels in a row produced by subtracting the data of FIG. 5 from that of FIG. 4 and adding a constant intensity level to the difference.

Curve Fitting. In one embodiment of the invention, correction of the intensity levels of the pixels in a column or row is begun by sequentially sampling those measured levels. A curve of a continuous distribution of intensities is generated from the measured data by known curve fitting techniques. The intensities predicted by the generated curve are then subtracted, position for position, from the measured pixel intensity data. Thereafter, an average intensity level is preferably added to the difference of intensity levels obtained in the substraction to produce a corrected intensity at each pixel in the subject column or row. An example of this noise-reduction technique is illustrated in FIGS. 4–6.

Figure 4:
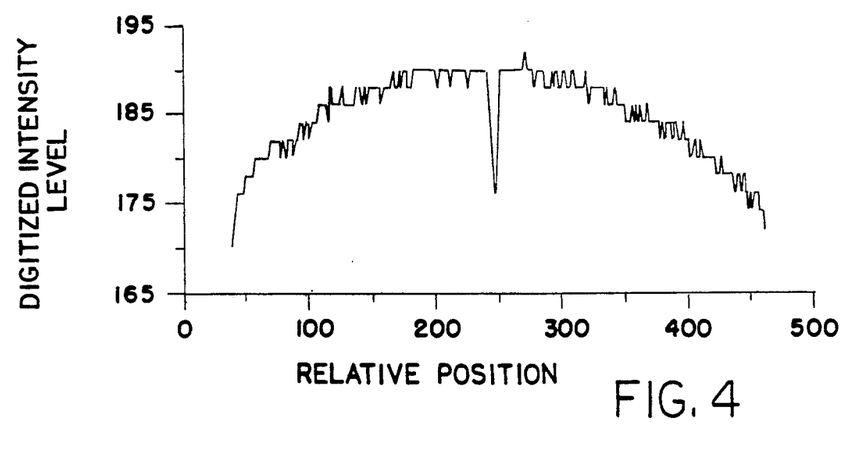
FIG. 4 is a graph of uncorrected digitized intensity level information for pixels in a row taken from a wafer image obtained according to the invention.

In FIG. 4, the digitized pixel intensity levels along one row of pixels are plotted as a function of position along the row. The ordinate represents a range of gray levels. The wafer from which the information of FIG. 4 was derived included a single isolated contrast variation near the center of the row. (In this and other techniques explained below, the edges of the wafer have been identified and background image pixels have been discarded. The information plotted is limited to wafer image information.) A useful technique for generating an intensity level distribution curve from the data of FIG. 4 is the well-known least squares estimation employing a polynomial of suitable order. A second order polynomial of the form shown in Equation (2) is useful for this purpose.

$$y(i,j) = a_1 * j^2 + a_2 * j + a_3 + b \tag{2}$$

In Equation (2), the gray level y(i,j) is the intensity level of the pixel at position (i,j). Equation (2) represents a distribution along a row, i.e. where i is unvarying. The term b is the uncorrelated noise in the distribution.

FIG. 5 graphically illustrates a calculated, digitized distribution of intensity levels resulting from fitting, by the least squares technique, of a curve to the information from FIG. 4. In FIG. 6, the difference obtained by subtracting the curve of FIG. 5 from the curve of FIG. 4 is plotted. In FIG. 6, the gray level has been adjusted to an average value (170) by adding to the difference between FIGS. 4 and 5 the intensity level of the pixel in FIG. 4 that lies at the left end of the row. FIG. 6, when compared to FIG. 4, shows that the effects of illumination non-uniformities have been substantially removed. Variations in intensity levels in FIG. 6 appear to result from other noise sources, except for the substantial central variation that is the contrast information of interest. The improved ability in FIG. 6, compared to FIG. 4, to detect the desired information is readily apparent.

In applying the curve-fitting technique, we have found that good results can be obtained even if every second row and/or column of pixels is omitted from the calculation of the theoretical intensity distribution. In addition to the row and column omissions, every second pixel intensity in a row or column may also be omitted from the curve-fitting calculation without introducing serious error into this intensity correction step. These omissions reduce the amount of computational time to complete the correction step. If the lighting source is stable and each wafer can be placed precisely in the same position for inspection, the correction information of FIG. 5 may be repeatedly used as a series of wafers are inspected. This measure can save considerable computational time. However, we have found that the characteristics of the preferred video camera introduce some instabilities between inspections. Because of those circumstances, the intensity distribution correction curves are preferably calculated for each wafer that is inspected.

Figure 7:
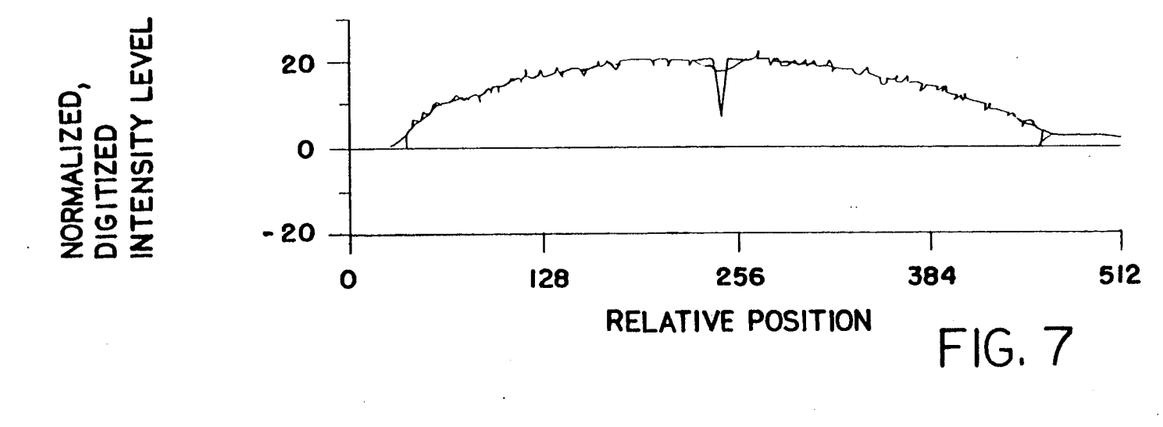
FIG. 7 is a graph of uncorrected, digitized intensity level information for pixels in a row taken from a wafer image obtained according to the invention overlaid with an estimated intensity level distribution produced by low pass filtering of the uncorrected intensity levels.

Linear Filtering. An alternative method of correcting pixel intensity information to reduce noise caused by non-uniformities in illumination employs linear filtering. Linear filtering is readily accomplished through the use of fast Fourier transform algorithms and a convolution step. FIG. 7 shows both the uncorrected, digitized intensity data for a single row of pixels and a smoother intensity distribution produced as the result of linear filtering. Both of these curves in FIG. 7 have been adjusted or normalized by subtracting the gray level value, i.e. the intensity value, at the left end of the row from all of the other intensity values in the row.

Figure 8:
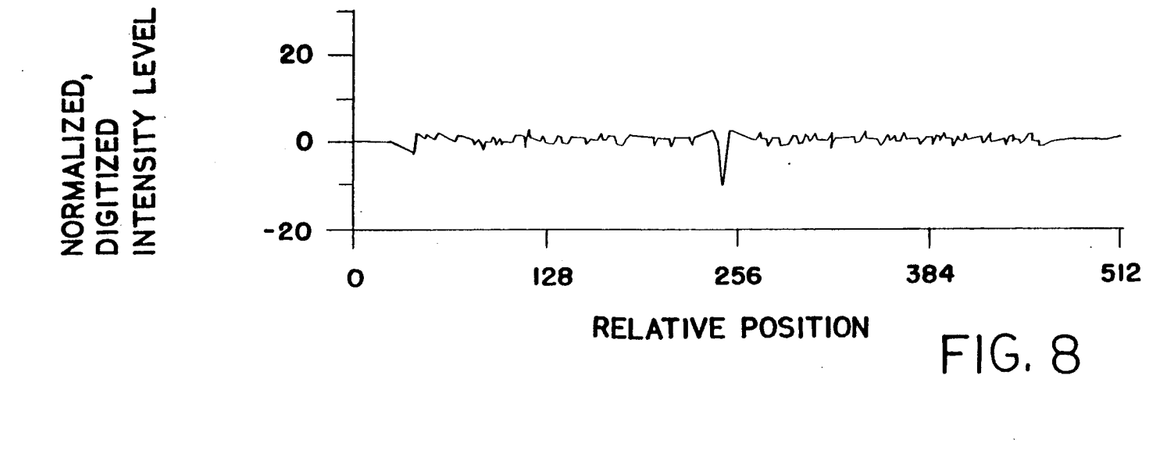
FIG. 8 is a graph of corrected, digitized intensity level information for pixels in a row produced by subtracting the estimated intensity level distribution of FIG. 7 from the uncorrected intensity information of FIG. 7.

In order to accomplish the linear filtering, a low pass filtering characteristic is first chosen. We have used a sixty four point Gaussian filter having a standard deviation of ten. The Fourier transform of this filter characteristic can be easily calculated using a conventional Fast Fourier Transform (FFT) algorithm. Subsequently, the FFT of the raw intensity value distribution is calculated. Thereafter, the two FFT's are multiplied and the inverse FFT of the product is calculated. This inverse FFT curve is the relatively smooth curve shown in FIG. 7. The difference between the inverse FFT curve and the raw data is calculated to produce the light intensity distribution shown in FIG. 8. Thereafter, that distribution can be adjusted upward to restore an average pixel intensity similar or equal to the uncorrected intensity of the leftmost pixel in the row.

LOCATION OF CONTRAST VARIATIONS

If the pixel intensity is corrected before searching for isolated contrast variations, then an illumination correction step, such as one of the two alternatives just described, is carried out. Alternatively, correction for light intensity variations can be an inherent part of the search for isolated contrast variations on the surface of the wafer. In that latter event, neither of the explicit intensity corrections just described is performed. In the former case, isolated contrast variations are found by sequentially examining the corrected intensity levels of pixels that are geometrically related in the wafer image, such as pixels lying contiguous to each other in a row. In the latter situation, the statistical variations of light intensities in groups of pixels representing various regions of the surface of the wafer are examined to identify contrast variations.

Edge Detection. After any explicit corrections for non-uniformities in illumination, the pixels are searched for abrupt intensity level changes indicating the entry into or the exit from an area of contrast variation. Techniques for searching visual images for contrast variations are well-known and are generally referred to as edge detection techniques. Edge detection techniques are discussed, among other sources, in volume 2 of Digital Picture Processing by Rosenfeld and Kak, cited above, and incorporated herein by reference. In the inspection process, it is important to establish the complete boundary and area of each contrast variation since that area, rather than the variation boundary or location, is of primary concern. An incomplete or discontinuous boundary makes calculation of the contrast area difficult or impossible. We prefer a two-step process of searching the pixels for both edge strength, i.e. a measure of the abruptness of a change in gray level, and relative intensity level.

In the first step of the two-step search, the corrected intensities of pixels are sequentially sampled in a row and an edge value is calculated for each pixel. Preferably, the edge value in a row is calculated from Equation (3).

$$\text{edge value} \\ (i,j) = g(i,j-2) + 2*g(i,j-1) - 2*g(i,j) - g(i,j+1) \quad (3)$$

According to Equation (3), the edge value is calculated in a row of pixels by comparing the intensities of the two pixels to the left of the pixel of interest with the intensities of both the pixel of interest and of the pixel to the right of the pixel of interest. An edge threshold is established for the edge value by inspecting wafers having no contrast variations or having isolated contrast variations of known dimensions. When the calculated edge value crosses over that edge threshold, an indication is given that an area of a contrast variation may have been entered or exited. Which of those events has taken place depends upon the state of the edge value at the time the threshold transition takes place. The direction of the threshold transition depends on whether the wafer is predominantly light in color with dark contrast variations or the opposite.

In any case, when the edge value makes a transition from one side of the edge threshold to the other, indicating possible entrance into a region of contrast variation, a low intensity level detector is activated. This low intensity level detector provides a second threshold test. When the low intensity level detector is activated and the intensity level of a pixel of interest falls on a preselected side of an established intensity threshold level, then that pixel is flagged as falling within a contrast variation. The low intensity level detector is deactivated when the calculated edge value makes a second transition across the edge threshold. That second edge threshold transition is opposite in direction from the first transition.

In understanding the foregoing method, it is important to note that the edge value is calculated based upon rates of change of pixel intensities as pixels in a row are sequentially examined. When a region of potential interest is located, then the intensities of individual pixels are compared against the low intensity level detector threshold to determine whether a contrast variation has actually been identified. This two-step searching of intensities helps achieve the goal of establishing continuous boundaries that circumscribe isolated contrast variations on the inspected surface.

The degree of confidence in the results produced by the two-step searching method can be improved by searching pixels both in rows and in columns. Pixels that are flagged as falling within areas of contrast variations preferably have their intensity levels adjusted to a first fixed value. Likewise, all other pixels preferably have their intensity levels adjusted to second fixed value that is significantly different from the first fixed value. These adjustments place the search results in a binary, digital format, making additional manipulation of the search results easier.

Statistical Detection. An alternative method for searching pixels to locate isolated contrast variations employs small regions of the wafer image, each region including a limited number of pixels. This method does not require explicit correction of the pixels for non-uniformities in illumination. Rather, this method employs statistical measures to identify contrast variations. The statistical measures inherently correct for non-uniformities in illumination.

Figure 9:
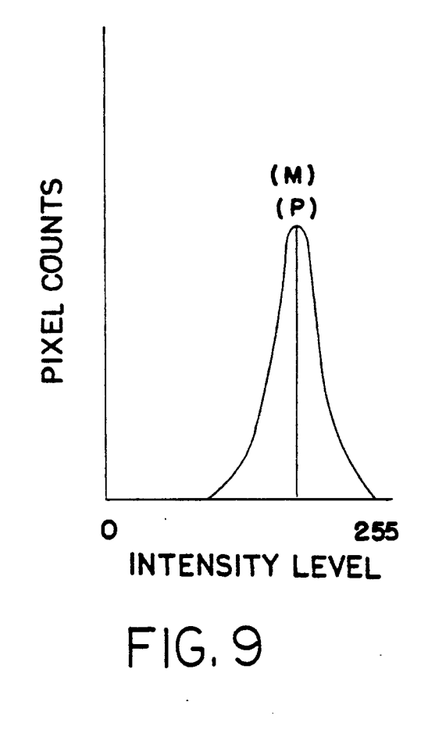
FIG. 9 is a graph of the distribution of pixel intensities for a region on wafer having uniform contrast.
Figure 10:
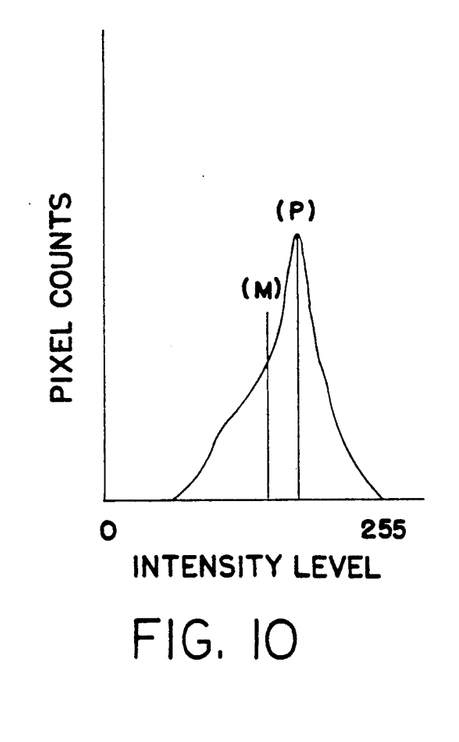
FIG. 10 is a graph of the distribution of pixel intensities for a region on a wafer including a contrast variation.

The statistical contrast variation identification process can be understood by referring to FIGS. 9 and 10. In FIG. 9, the statistical distribution of pixel intensity levels for a relatively small region of a wafer image free of contrast variations is plotted. The distribution is approximately Gaussian and is symmetrical about the intensity level that most frequently occurs in the region. In FIG. 10, the distribution of intensity levels is plotted for a region containing a contrast variation. The symmetry of the distribution of FIG. 9 is not present in FIG. 10. In addition, the mean intensity level (M) of FIG. 10 is shifted from the intensity level that most frequently occurs (P) in the region of FIG. 10. The disparities between the distributions of FIGS. 9 and 10, in statistical terms are that the standard deviation of the distribution of FIG. 10 is larger than that of FIG. 9 and the difference between the mean and peak values (MPD) of the gray level intensities has also increased in FIG. 10 compared to FIG. 9. The direction of increase of the MPD depends upon whether the contrast variation region is dark compared to its background or vice versa.

These observed statistical changes can be employed to determine whether various regions of the wafer surface contain isolated contrast variations. Generally, the standard deviation and the absolute value of the MPD are compared to established thresholds to determine whether a particular region includes at least part of a contrast variation. If so, the pixels falling within regions in which contrast variations are located and having intensities falling on a selected side of the mean intensity for the region, have their intensities reset to a first fixed value. That first value indicates a pixel within a contrast variation. Pixels not so identified, whether within or outside a region containing a contrast variation, have their associated intensity levels set to a different, second fixed value.

In practice, the process just described preferably begins with identification of pixels from the background image and from the wafer image and the discarding of the background image as described above. Thereafter, the wafer image is segmented into regions, each region containing a fixed number of contiguous pixels. Generally, when the pixels are organized in rows and columns, each region represents a rectangular area on the wafer. For example, a region selected as a standard size for an inspection may represent a square area and contain sixty four pixels, eight pixels lying along each side of the represented area. When a circular wafer is being inspected, the segmentation may result in discarding some of the pixels representing the peripheral areas of the wafer. All regions of the selected standard size lying outside the periphery of the wafer are ignored.

Within each region, the intensity level that most frequently occurs is determined. That peak intensity or gray level is designated as P. All intensity levels are summed in each region and divided by the number of pixels in the region to obtain the mean intensity value M for the region. The difference between the means and peak intensity values in each region, the MPD, is calculated. Preferably, the absolute value of the MPD is determined so that the mathematics of the search need not be altered depending upon whether the contrast variations are relatively light against a dark wafer surface or are relatively dark against a light wafer surface. The standard deviation of the intensity levels in each region is calculated. Identical calculations are made for all regions produced in the segmentation of the wafer image.

Preferably, the standard deviations of all the regions are averaged. This wafer average standard deviation is used to normalize the standard deviations for all regions by dividing each regional standard deviation by the wafer average standard deviation. This normalization step assists in eliminating the effects of noise, including noise attributable to non-uniformities in illumination. However, the normalization step can decrease the sensitivity of the method if isolated contrast variations of large area exist on the wafer surface. These large area contrast variations produce a relatively large wafer average standard deviation.

The regional standard deviation and MPD's are compared against threshold values established by testing wafers having no discernable isolated contrast areas. If both the standard deviation and MPD, i.e. the difference intensity level, for a region fall on a preselected side of their respective thresholds, the region is identified as including at least some pixels falling within a contrast variation. If neither or only one of the tested parameters falls on a preselected side of its respective threshold, the region being examined is considered not to include any part of a contrast variation. In that latter case, the intensities of all the pixels in the region are preferably set to a first fixed value, such as zero. Where a region is identified as containing a contrast variation, the pixel intensities in the region are compared to the mean value for the region. The pixels having intensities falling on a selected side of the mean are considered as falling within a contrast variation. The intensity levels of those pixels are preferably set to a second fixed value that is significantly different from the first fixed value. The intensity levels of the other pixels in the region are set to the first value. This step reduces the wafer image to binary information that is particularly easy to use in the subsequent steps of the method. The side of the mean intensity level that indicates the presence of a contrast variation depends on the hue of the wafer. For dark variations on a light colored wafer, an intensity level below the mean indicates a contrast variation. For dark wafers, the test is reversed.

When the steps described above have been completed, regardless of which alternative method is employed, an image of the contrast variations is obtained. The pixels identified as representing areas of contrast lie in isolated groups of contiguous pixels, each representing a contrast variation on the wafer surface. In order to determine the area of each isolated contrast variation, the boundaries of each contiguous group of identified pixels must be determined. Once the boundary of a particular pixel group, i.e. variation, is determined, the area of that variation can be determined simply by counting the number of pixels within the boundary. Each pixel is related to and is representative of a known area on the wafer surface. That correlated area is used with the counted number of pixels within a contiguous group to determine the actual area of each contrast variation.

In order to locate the boundaries of a contrast variation using the pixel information, the component labeling technique, which is known in the art of digital image processing, is preferably employed. The component labeling technique is discussed in Digital Picture Processing by Rosenfeld and Kak, volume 2, pp. 240-257, which is incorporated herein by reference. The cited excerpt from that source contains an explanation of the use of the component labeling technique to determine the boundary of a region in a digital image. In the technique, the boundaries of closed areas (assumed to be simply connected) are determined by beginning from a known point (pixel) on a boundary and then by sampling neighboring points (pixels) to identify additional boundary points. An eventual return to the initial point indicates closure of the boundary and complete identification of the pixels within the area enclosed by the boundary. In the invention, each boundary encloses a contiguous group of pixels that have been identified as lying within an isolated contrast variation. If, as preferred, the search results have been placed in binary form, then the identified pixels all have a "high" value and the other pixels have a "low" value, or vice versa.

Additional portions of the Rosenfeld and Kak reference describe determination of the shape of an area enclosed by a boundary. In most applications of the inspection method, the shape of the contrast variations is not of importance. Rather, we prefer to treat each contrast variation as if it were circular in shape. Based on that assumption and the knowledge of the area of a contrast variation, an equivalent diameter of the variation can be calculated.

The inspection data thus obtained consist of the number of isolated contrast variations on a wafer or other article surface and the area and equivalent diameter of each of those variations. This information can be used in deciding whether a wafer meets a particular standard. Because the inspection data produced are quite detailed, complex criteria for deciding whether a wafer is acceptable for a particular purpose can be devices and employed. For example, a wafer containing several, relatively small isolated contrast variations might be commercially acceptable for a particular purpose. However, a single isolated contrast variation of the same total area as the several small contrast variations, might make the wafer unacceptable for the same purpose. This result follows from an assumption that there is an upper limit to the percentage of the surface area of an acceptable wafer that can be occupied by contrast variations. Accordingly, different acceptability criteria apply to articles of different sizes.

Examples of criteria for determining the acceptability of a wafer for a particular purpose are illustrated in Tables 1 and 2. In Table 1, contrast variations are assigned one of categories I-IV according to their equivalent diameter, i.e. effectively, their area. In Table 2, exemplary acceptability criteria for circular wafers of various diameters including variations of categories I-IV are listed. In applying the criteria of Table 2, the quantity of the contrast variations in each of the respective size categories is sequentially compared to the limits, column by column. For example, in the first column of Table 2, for a four inch diameter wafer, as many as two contrast variations having sizes within Group I together with three variations having sizes falling within Group IV can be tolerated, provided there are no contrast variations having sizes falling within either of Groups II and III. If those acceptability standards are not met, then the standards of the second column are applied. That is, an examination of the contrast variations is made to determine if there are no more than four Group II size and one Group IV size variations, without the presence of any variations having sizes falling within Groups I and III. Likewise, the other criteria set forth are applied, if necessary, to decide whether a wafer meets any of the acceptability criteria. When the criteria of any column are met, the testing is ended and the tested wafer is accepted. If all applicable criteria are applied without success, then the tested wafer is rejected for the application on which the criteria are based. In the latter case, a second, different set of criteria may be applied to decide whether a wafer that is suitable for one purpose might be unsuitable for another purpose. These tests may be combined with actuating equipment that sequentially feeds wafers to an inspection station, like that shown in FIG. 1, and that directs inspected wafers to one of several different possible destinations depending upon the inspection results.

The invention has been described with respect to certain preferred embodiments. Various modifications and additions will be apparent to those of skill in the art. Accordingly, the scope of the invention is limited solely by the following claims.

TABLE 1

Classification of Contrast Variations by Equivalent Diameter

| Category | Equivalent Diameter, d, in mm |
|---|---|
| Group I | $0.6 < d < 0.5$ |
| Group II | $0.5 < d < 0.4$ |
| Group III | $0.4 < d < 0.3$ |
| Group IV | $0.3 < d$ |

TABLE 2

Exemplary Inspection Criteria For Circular Wafers

| Nominal Wafer Diameter = 4 in. (102 mm) | | | | | | | |
|---|---|---|---|---|---|---|---|
| Group I | 2 | 0 | 0 | 0 | 0 | 0 | 0 |
| Group II | 0 | 4 | 2 | 0 | 0 | 0 | 0 |
| Group III | 0 | 0 | 3 | 6 | 4 | 2 | 0 |
| Group IV | 3 | 1 | 0 | 1 | 3 | 7 | 11 |
| Nominal Wafer Diameter = 3 in. (7.6 mm) | | | | | | | |
| Group I | 1 | 0 | 0 | 0 | 0 | 0 | 0 |
| Group II | 0 | 2 | 1 | 0 | 0 | 0 | 0 |
| Group III | 0 | 0 | 2 | 3 | 2 | 1 | 0 |
| Group IV | 2 | 1 | 0 | 1 | 2 | 4 | 6 |
| Nominal Wafer Diameter = 2 in. (51 mm) | | | | | | | |
| Group I | 1 | 0 | 0 | | | | |
| Group III | 0 | 1 | 0 | | | | |
| Group IV | 0 | 1 | 3 | | | | |
| Nominal Wafer Diameter = 1 in. (25 mm) | | | | | | | |
| Group III | 1 | 0 | | | | | |
| Group IV | 0 | 2 | | | | | |

We claim:

1. A method of inspecting a surface of an article for isolated contrast variations, comprising:
   illuminating a surface of an article;
   forming a surface image from the light reflected from said surface, said surface image being composed of a plurality of pixels, said pixels comprising digitized electrical signals each indicative of the relative intensity level of light reflected from a particular portion of said surface;
   comparing the intensity levels of at least some of the pixels to a predetermined intensity threshold to identify pixels corresponding to portions of said surface contrasting with other portions of said surface;
   determining the number of isolated regions of contrast variation on said surface and determining the magnitude of the space occupied by the area of each of said isolated regions of contrast variation from the number of pixels within each isolated region of contrast variation; and applying acceptability criteria based upon the number of isolated regions of contrast variation and the magnitudes of the respective areas of the isolated regions of contrast variation to decide whether the article is acceptable for a particular use.

2. A method of inspecting a surface for isolated contrast variations, comprising:

disposing an article of a known shape of a background, said background contrasting with a surface of the article;

illuminating the surface of the article and a portion of said background adjacent to the periphery of said article;

forming a background and surface image, said background and surface image being composed of a plurality of pixels, the pixels comprising digitized electrical signals each indicative of the relative intensity level of light reflected from a particular portion of the background or the surface;

locating the periphery of said article in the background and surface image;

discarding from further consideration pixels representing areas lying outside said periphery;

correcting the intensity levels of the remaining pixels in the article image to compensate for non-uniformities in the illumination of the surface;

comparing the corrected intensity levels of at least some of the pixels to a predetermined intensity threshold to identify pixels corresponding to portions of the surface contrasting with other portions of the surface;

determining from the identified pixels the number of isolated contrast variations on the surface and the area of each of the isolated contrast variations; and applying acceptability criteria based upon the number and respective areas of the isolated contrast variations to decide whether the article is acceptable for a particular use.

3. The method of claim 2 wherein said article has a known shape, including identifying a sufficient number of pixels to determine the position of the periphery of said article without identifying every pixel lying along said periphery.

4. A method of inspecting a surface for isolated contrast variations, comprising;

disposing an article of a known shape on a background, the background contrasting with a surface of the article, the article being generally circular;

illuminating the surface of the article and a portion of the background adjacent to the periphery of the article;

forming a background and surface image from the light reflected from the portion of the background and from the surface, the background and surface image being composed of a plurality of pixels, the pixels comprising digitized electrical signals each indicative of the relative intensity level of light reflected from a particular portion of the background or the surface;

locating the periphery of the article in the background and surface image, including identifying a sufficient number of pixels to determine the position of the periphery of the article without identifying every pixel lying along the periphery, including sequentially examining the intensities of pixels lying along each of two orthogonal directions, locating along each of said two directions two pixels that represent areas lying contiguous to or partially on the periphery of said article, and determining the location of the center and radius of the article from the two pairs of said two pixels;

discarding from further consideration pixels representing areas lying outside the periphery;

comparing the corrected intensity levels of at least some of the pixels to a predetermined intensity threshold to identify pixels corresponding to portions of the surface contrasting with other portions of the surface;

determining from the identified pixels the number of isolated contrast variations on the surface and the area of each of the isolated contrast variations; and applying acceptability criteria based upon the number and respective areas of the isolated contrast variations to decide whether the article is acceptable for a particular use.

5. A method of inspecting a surface of an article for isolated contrast variations, comprising:

illuminating a surface of an article;

forming a surface image from the light reflected from the surface, the surface image being composed of a plurality of pixels, the pixels comprising digitized electrical signals each indicative of the relative intensity level of light reflected from a particular portion of the surface, the pixels being organized in orthogonal rows and columns representing corresponding portions of said surface;

correcting the intensity levels of the pixels in the article image to compensate for non-uniformities in the illumination of the surface by fitting the distribution of intensity levels along one of said rows or columns to a polynomial distribution to provide predicted intensity levels and adjusting the intensity level of each pixel in said row or column by the predicted intensity level for that pixel from the polynomial distribution;

comparing the corrected intensity levels of at least some of the pixels to a predetermined intensity threshold to identify pixels corresponding to portions of the surface contrasting with other portions of the surface;

determining from the identified pixels the number of isolated contrast variations on the surface and the area of each of the isolated contrast variations; and applying acceptability criteria based upon the number and respective areas of the isolated contrast variations to decide whether the article is acceptable for a particular use.

6. The method of claim 5 including adding an average intensity level to each difference intensity level obtained by said subtracting step to produce corrected pixel intensities.

7. The method of claim 5 wherein said polynomial is a second order polynomial.

8. A method of inspecting a surface of an article for isolated contrast variations, comprising:

illuminating a surface of an article;

forming a surface image from the light reflected from the surface, the surface image being composed of a plurality of pixels, the pixels comprising digitized electrical signals each indicative of the relative intensity level of light reflected from a particular portion of the surface, the pixels being organized in orthogonal rows and columns representing corresponding portions of said surface;

correcting the intensity levels of the pixels in one of said rows or columns to compensate for non-uniformities in the illumination of the surface by:
(i) normalizing the intensity levels by subtracting the intensity level of the first pixel in said row or column from the intensity level of each pixel in said row or column,
(ii) convolving the normalized intensity levels with a smoothing, low pass filter to produce a convolved light intensity distribution along said row or column to provide predicted intensity levels, and
(iii) adjusting the intensity level of each pixel in said row or column by the predicted intensity level from the convolution for that pixel;

comparing the corrected intensity levels of at least some of the pixels to a predetermined intensity threshold to identify pixels corresponding to portions of the surface contrasting with other portions of the surface;

determining from the identified pixels the number of isolated contrast variations on the surface and the area of each of the isolated contrast variations; and applying acceptability criteria based upon the number and respective areas of the isolated contrast variations to decide whether the article is acceptable for a particular use.

9. The method of claim 8 including adding an average intensity level to each difference intensity level obtained by said subtracting step to produce corrected pixel intensities.

10. The method of claim 8 including convolving said normalized intensity levels with said low pass filter by computing the Fourier transform of each of said normalized intensity levels and said filter, multiplying the transforms and computing the inverse Fourier transform of the product.

11. A method of inspecting a surface of an article for isolated contrast variations, comprising:
illuminating a surface of an article;
forming a surface image from the light reflected from the surface, the surface image being composed of a plurality of pixels, the pixels comprising digitized electrical signals each indicative of the relative intensity level of light reflected from a particular portion of the surface, the pixels being organized in orthogonal rows and columns representing corresponding portions of said surface;
comparing the intensity levels of at least some of the pixels to a predetermined intensity threshold to identify pixels corresponding to portions of the surface contrasting with other portions of the surface, wherein comparing comprises, for each row,
calculating an edge intensity value for each pixel from the intensity level of the pixel and the intensity level of neighboring pixels in the row,
comparing the edge intensity value to an edge threshold,
activating an intensity threshold detector when said edge intensity value changes from a first level on one side of said edge threshold to a second level on the other side of said edge threshold and
comparing the intensity level of each pixel to said intensity threshold when said threshold detector is activated;

determining from the identified pixels the number of isolated contrast variations on the surface and the area of each of the isolated contrast variations; and applying acceptability criteria based upon the number and respective areas of the isolated contrast variations to decide whether the article is acceptable for a particular use.

12. A method of inspecting a surface of an article for isolated contrast variations, comprising:
illuminating a surface of an article;
forming a surface image from the light reflected from the surface, the surface image being composed of a plurality of pixels, the pixels comprising digitized electrical signals each indicative of the relative intensity level of light reflected from a particular portion of the surface, the pixels being organized in orthogonal rows and columns representing corresponding portions of the surface;
comparing the intensity levels of at least some of the pixels to a predetermined intensity threshold to identify pixels corresponding to portions of the surface contrasting with other portions of the surface, including, for each row,
calculating an edge intensity value for each pixel from the intensity level of the pixel and the intensity level of neighboring pixels in the row, said edge intensity value for a pixel of interest in said row being calculated as:
(a) the sum of
(i) the intensity level of the pixel lying in said row two pixels on one side of the pixel of interest, and
(ii) twice the intensity level of the pixel lying in said row one pixel on the one side of the pixel of interest; minus
(b) the sum of
(iii) twice the intensity level of the pixel of interest, and
(iv) the intensity level of the pixel lying in said row one pixel on the other side of the pixel of interest;
comparing the edge intensity value to an edge threshold,
activating an intensity threshold detector when the edge intensity value changes from a first level on one side of the edge threshold to a second level on the other side of the edge threshold and
comparing the intensity level of each pixel to the intensity threshold when the threshold detector is activated;
determining from the identified pixels the number of isolated contrast variations on the surface and the area of each of the isolated contrast variations; and
applying acceptability criteria based upon the number and respective areas of the isolated contrast variations to decide whether the article is acceptable for a particular use.

13. A method of inspecting a surface of an article for isolated contrast variations, comprising:
illuminating a surface of an article;
forming a surface image from the light reflected from the surface, the surface image being composed of a plurality of pixels, the pixels comprising digitized electrical signals each indicative of the relative intensity level of light reflected from a particular portion of the surface, the pixels being organized in orthogonal rows and columns representing corresponding portions of the surface;

comparing the intensity levels of at least some of the pixels to a predetermined intensity threshold to identify pixels corresponding to portions of the surface contrasting with other portions of the surface, including, for each row,
  calculating an edge intensity value for each pixel from the intensity level of the pixel and the intensity level of neighboring pixels in the row,
  comparing the edge intensity value to an edge threshold,
  activating an intensity threshold detector when the edge intensity value changes from a first level on one side of the edge threshold to a second level on the other side of the edge threshold,
  deactivating said threshold detector when said edge intensity value changes from said second level on said other side of said edge threshold to said first level on said one side of said edge threshold, and
  comparing the intensity level of each pixel to the intensity threshold when the threshold detector is activated;
determining from the identified pixels the number of isolated contrast variations on the surface and the area of each of the isolated contrast variations; and
applying acceptability criteria based upon the number and respective areas of the isolated contrast variations to decide whether the article is acceptable for a particular use.

14. The method of claim 13 including identifying as contrasting each pixel having an intensity falling on a preselected side of said intensity threshold when said intensity threshold detector is activated.

15. The method of claim 13 wherein the intensity level of each pixel, when said threshold detector is activated, not falling on said preselected side of said intensity threshold, is altered to a first preselected value.

16. The method of claim 15 wherein the intensity level of each pixel, when said threshold detector is activated, falling on said preselected side of said intensity threshold, is altered to a second preselected value that is different from said first preselected value.

17. The method of claim 15 wherein the intensity level of each pixel, when said threshold detector is deactivated, is altered to said first preselected value.

18. A method of inspecting a surface of an article for isolated contrast variations, comprising:
  illuminating a surface of an article;
  forming a surface image from the light reflected from the surface, the surface image being composed of a plurality of pixels, the pixels comprising digitized electrical signals each indicative of the relative intensity level of light reflected from a particular portion of said surface, said pixels being organized in orthogonal rows and columns representing corresponding portions of said surface;
  grouping said rows and columns into regions, each region containing a plurality of contiguous pixels,
  calculating the means and standard deviation of the intensity levels of the pixels with each region,
  identifying the most frequently occurring intensity level in each region, and
  calculating a difference intensity level between the most frequently occurring and mean intensity levels in each region;
  comparing the intensity levels of at least some of the pixels to a predetermined intensity threshold to identify pixels corresponding to portions of the surface contrasting with other portions of the surface, wherein comparing comprises comparing said difference intensity level of each region to said intensity threshold and comparing said standard deviation of the intensity levels of each region to a second predetermined threshold;
  determining from the identified pixels the number of isolated contrast variations on said surface and the area of each of the isolated contrast variations; and
  applying acceptability criteria based upon the number and respective areas of the isolated contrast variations to decide whether the article is acceptable for a particular use.

19. The method of claim 18 wherein at least part of a region is identified as including at least part of an isolated contrast region if both the absolute value of the difference intensity level and the standard deviation of the intensity level for the region fall on a preselected side of their respective thresholds.

20. The method of claim 19 including comparing the intensity level of each pixel within a region identified as including at least part of an isolated contrast region with the mean intensity level for that region and identifying as lying within said region each pixel having an intensity level lying on a preselected side of said mean intensity.

21. The method of claim 20 including altering to a first preselected value the intensity level of each pixel identified as lying within an isolated contrast variation.

22. The method of claim 21 including altering to a second preselected value, different from said first preselected value, (i) the intensity level of each pixel within each region identified as not including at least part of a contrast variation and (ii) the intensity level of each pixel within a region including at least part of an isolated contrast variation, but having an intensity not lying on the preselected side of said mean intensity.

23. A method of inspecting a surface of an article for isolated contrast variations comprising
  illuminating a surface of an article;
  forming a surface image from the light reflected from the surface, the surface image being composed of a plurality of pixels, the pixels comprising digitized electrical signals each indicative of the relative intensity level of light reflected from a particular portion of the surface;
  comparing the intensity levels of at least some of the pixels to a predetermined intensity threshold to identify pixels corresponding to portions of the surface contrasting with other portions of the surface; and
  applying acceptability criteria based upon the number of isolated regions of contrast variation and the magnitudes of the respective areas of the isolated regions of contrast variation to decide whether the article is acceptable for a particular use, including determining the number of isolated regions of contrast variation by finding the boundaries of each contiguous group of identified pixels and finding the magnitude of the space occupied by the area of each of the isolated regions of contrast variation by counting the number of pixels within each contiguous group.

24. A method of inspecting a surface of an article for isolated contrast variations, comprising:
  illuminating a surface of an article;

forming a surface image from the light reflected form the surface, the surface image being composed of a plurality of pixels, the pixels comprising digitized electrical signals each indicative of the relative intensity level of light reflected from a particular portion of the surface;

comparing the intensity level of at least some of the pixels to a predetermined intensity threshold to identify pixels corresponding to portions of the surface contrasting with other portions of the surface;

determining the number of isolated regions of contrast variation on the surface and magnitude of the space occupied by the area of each of the isolated regions of contrast variation from the number of pixels within each isolated region of contrast variation;

applying acceptability criteria based upon the number of isolated regions of contrast variation and the magnitudes of the respective areas of the isolated regions of contrast variation in each category to decide whether the article is acceptable for a particular use, including segregating the regions of contrast variation into a plurality of categories according to the magnitude of the space occupied by the area of each region and counting the number of isolated regions of contrast variation falling within each category.

25. An apparatus for identifying the quantity and respective areas of isolated contrast variations on the surface of an article, comprising:

means for substantially uniformly illuminating a surface of an article;

means for forming a surface image of said surface composed of a plurality of pixels, said pixels comprising digitized electrical signals each indicative of the relative intensity level of the light reflected from a particular portion of said surface;

means for searching said pixels to identify isolated regions of contrast variation on said surface and for determining the magnitude of the space occupied by the area of each said region; and means for comparing the quantity of the isolated regions of contrast variation and the magnitude of the space occupied by of the areas of the isolated regions of contrast variation to acceptability criteria to decide whether the article is acceptable for a particular use.

26. An apparatus for identifying the quantity and respective areas of isolated contrast variations on the surface of an article, comprising:

means for substantially uniformly illuminating a surface of an article, comprising a fluorescent lamp having a plurality of segments each substantially uniformly spaced from each other, the segments substantially uniformly illuminating the surface of the article;

means for forming a surface image of the surface composed of a plurality of pixels, the pixels comprising digitized electrical signals each indicative of the relative intensity level of the light reflected from a particular portion of said surface;

means for searching the pixels to identify regions of isolated contrast variation on the surface and for determining the magnitude of the space occupied by the area of each of the regions; and means for comparing the quantities and respective magnitude of the space occupied by the areas of the isolated regions of contrast variation to acceptability criteria to decide whether the article is acceptable for a particular use.

27. The apparatus of claim 26 wherein said means for forming an image comprises a video camera having a lens and said fluorescent lamp includes a central opening through which said lens may protrude.

28. The apparatus of claim 26 wherein said means for forming an image comprises a video camera.

29. The apparatus of claim 26 wherein said means for searching, for determining and for comparing comprises a computer.

* * * * *